United States Patent [19]
Gharibadeh

[11] Patent Number: 5,108,525
[45] Date of Patent: Apr. 28, 1992

[54] METHOD OF TWISTING AND HEAT SHRINKING A TUBULAR CATHETER MEMBER SECTION ONTO AN INNER MEMBER

[75] Inventor: Ramsin Gharibadeh, San Jose, Calif.

[73] Assignee: Advanced Cardiovascular Sytems, Inc., Santa Clara, Calif.

[21] Appl. No.: 521,103

[22] Filed: May 9, 1990

[51] Int. Cl.$^5$ ................. B32B 1/10; B29C 61/02
[52] U.S. Cl. ..................... 156/86; 156/294; 264/230; 264/295; 264/296; 604/96
[58] Field of Search ............ 264/230, 342 R, 295, 264/296, 275, DIG. 41, 500, 519, 322, 327; 156/86, 294

[56] References Cited

U.S. PATENT DOCUMENTS

| Re. 30,817 | 12/1981 | Loyd et al. | 156/294 |
| 2,396,635 | 3/1946 | Bogoslowsky | 264/DIG. 41 |
| 3,347,970 | 10/1967 | Hanna | 264/230 |
| 4,227,293 | 10/1980 | Taylor | 264/230 |
| 4,323,071 | 4/1982 | Simpson et al. | 604/28 |
| 4,792,047 | 12/1988 | Wood et al. | 264/296 |

Primary Examiner—Jan H. Silbaugh
Assistant Examiner—Brian J. Eastley
Attorney, Agent, or Firm—Crosby, Heafey, Roach & May

[57] ABSTRACT

A method for bonding a heat shrinkable tubular member to an inner member where a section of the tubular member is first twisted and then subjected to heat and tension to cause the twisted section to sealingly bond to an inner member disposed therein. The method is particularly directed to bonding the distal end of a balloon on an angioplasty catheter to an inner member.

3 Claims, 1 Drawing Sheet

METHOD OF TWISTING AND HEAT SHRINKING A TUBULAR CATHETER MEMBER SECTION ONTO AN INNER MEMBER

BACKGROUND OF THE INVENTION

This invention generally relates to a method of joining a heat shrinkable, tubular member to an inner member such as found in the construction of vascular catheters and particularly low-profile steerable catheters for angioplasty procedures.

In classic percutaneous transluminal coronary angioplasty procedures (PTCA), a guiding catheter having a preformed distal tip is first percutaneously introduced into the patient's arterial system and advanced therein until the distal tip of the guiding catheter is disposed in the appropriate ostium of the patient's coronary artery. A guidewire is preloaded within an inner lumen of a dilatation catheter and both are advanced through the previously positioned guiding catheter to the distal end thereof. The guidewire is first advanced out of the distal end of the guiding catheter into the patient's coronary anatomy until the distal end of the guidewire crosses the stenotic region to be dilated. The dilatation catheter is then slidably advanced out the distal tip of the guiding catheter over the guidewire into the patient's coronary artery until the balloon on the dilatation catheter is positioned within the stenosis. The balloon is inflated to a relatively high pressure (e.g. up to 8 atmospheres or more) to dilate the stenosis and then deflated and removed over the guidewire. For a detailed description of procedures, reference is made to U.S. Pat. No. 4,332,254 (Lundquist), U.S. Pat. No. 4,323,071 (Simpson-Robert), U.S. Pat. No. 4,411,055 (Simpson-Robert), U.S. Pat. No. 4,439,185 (Lundquist), U.S. Pat. No. 4,468,224 (Enzmann et al.), U.S. Pat. No. 4,516,972 (Samson), U.S. Pat. No. 4,538,622 (Samson et al.), U.S. Pat. No. 4,554,929 (Samson et al.), U.S. Pat. No. 4,569,347 (Frisbie), U.S. Pat. No. 4,571,240 (Samson et al.), U.S. Pat. No. 4,638,805 (Powell), U.S. Pat. No. 4,748,982 (Horzewski et al.), all of which are hereby incorporated herein in their entirety by reference thereto.

Steerable dilatation catheters with built-in or fixed guidewires or guiding members are frequently used because the deflated profile of such catheters are generally much smaller than conventional over-the-wire type dilatation catheter system described above having the same inflated balloon diameter. Further details of steerable fixed wire dilatation catheters may be found in U.S. Pat. No. 4,582,181 (Samson) which is hereby incorporated herein in its entirety by reference thereto. The lower profile of these catheters allows them to cross tighter lesions and to be advanced much deeper into the patient's coronary anatomy than over-the-wire type catheters.

With most dilatation catheters, the distal ends of the balloons are bonded to an inner guiding member or an inner tubular member by a suitable adhesive. However, this bond may require relatively large amounts of adhesive material, frequently making the catheter stiff at this bond location, particularly with steerable, fixed wire catheters.

What has been needed and heretofore unavailable is a method of sealingly bonding the distal end of the balloon on an intravascular catheter such as used is angioplasty procedures to an inner member so that the joint has a greater degree of flexibility and a lower profile. The present invention satisfies that need.

SUMMARY OF THE INVENTION

The present invention is directed to a method and system for joining a heat shrinkable, tubular member to an inner member such as found in dilatation catheters designed for performing intravascular procedures.

In accordance with the present invention a first mandrel is inserted into the inner lumen of a heat shrinkable outer tube from one end thereof, a second mandrel is inserted into the outer tube from the other end thereof with the opposed ends of the mandrels axially spaced from one another. An inner member to which the outer tube is to be bonded is disposed within the inner lumen of the outer tube at a location between the spaced apart ends of the mandrels. The two mandrels are preferably hollow with the inner member extending within the inner lumens of the hollow mandrels so as to expose the area of the inner member where the heat shrinkable outer tube is to be bonded.

In order to bond the outer tube to the inner member, the outer tube is releasably secured to the opposing spaced apart ends of the two mandrels, the releasably secured ends of the outer tube are axially rotated with respect to one another, while tension and heat are applied to the twisted portion, to cause the twisted portion of the heat shrinkable outer tube to heat shrink and bond to the exposed portion of the inner member. The result is a leak free bond at the high internal pressures normally encountered in PTCA procedures. Moreover, the location has improved flexibility and a much lower profile than prior adhesively bonded distal ends. These and other advantages of the present invention will become more apparent from the following detailed description thereof, when taken in conjunction with the accompanying exemplary drawings.

DETAILED DESCRIPTION OF THE INVENTION

Figure 1:
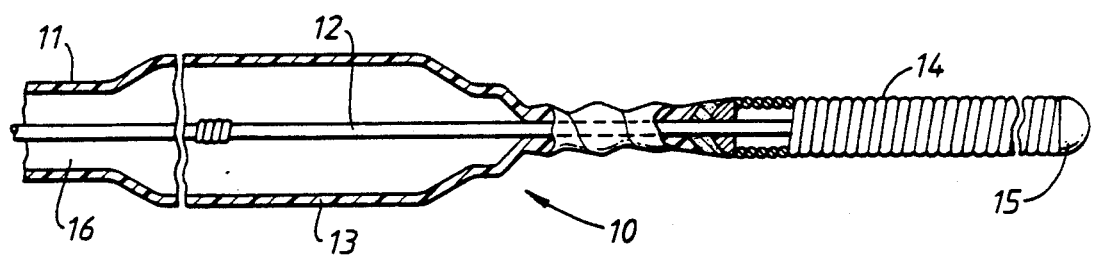
FIG. 1 is an elevational view, partially in section, of the distal end of a dilatation catheter embodying features of the invention.

Reference is made to FIG. 1 which schematically illustrates the distal end of a steerable dilatation catheter 10 embodying features of the present invention. The catheter 10 generally includes a tubular member 11 with a inner guiding member 12 disposed therein which extends through the inflatable relatively inelastic balloon 13 and out the distal end thereof. A flexible body, such as a coil 14, is secured to the portion of the guiding member which extends out of the distal end of the balloon 13 and has a rounded plug 15 on the distal portion thereof. The tubular member 11 extends proximally a considerable distance and the proximal end thereof is provided with an adaptor (not shown) as is conventional with angioplasty catheters to inject inflation fluid through the inner lumen 16 to the interior of the balloon 13.

Figure 2:
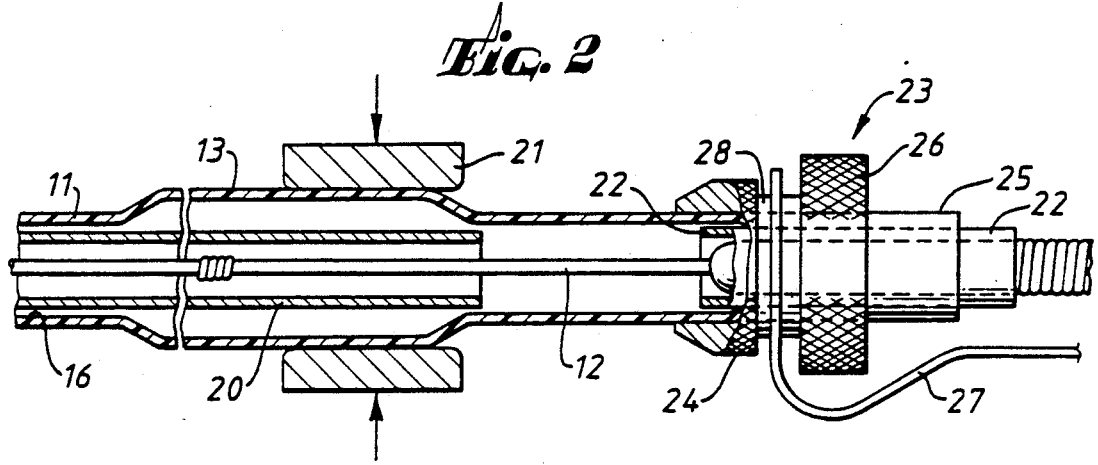
FIG. 2 is an elevation view, partially in section, illustrating the arrangement of the components for the method of the invention.
Figure 3:
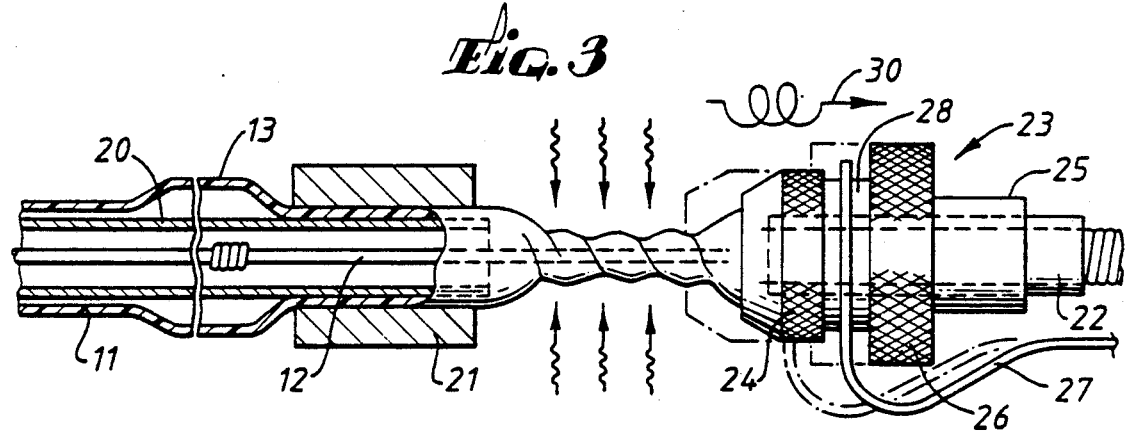
FIG. 3 is an elevation view, partially in section, illustrating the twisting and the heating steps in the method of the invention.
Figure 4:
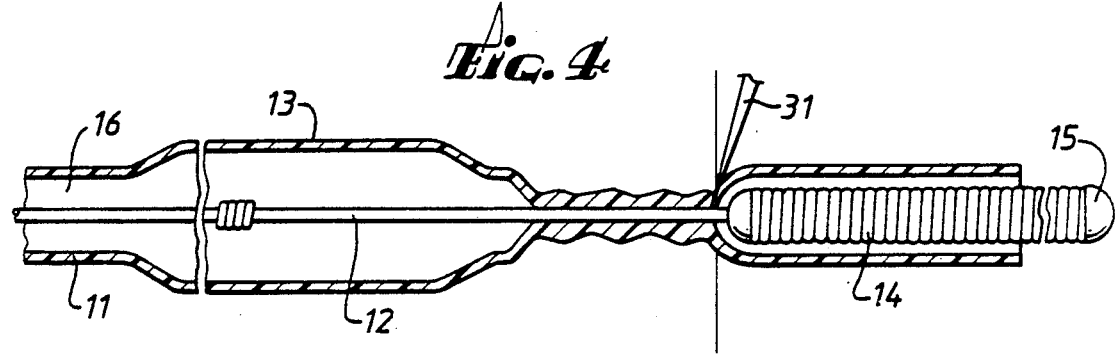
FIG. 4 is an elevation view, partially in section, illustrating the final step of the invention wherein excess tubing is removed.

The method and system for joining the distal end of the balloon to the inner guiding member is best illustrated in the sequence of FIGS. 2–4. As shown, a first hollow mandrel 20 is inserted into the relatively long inner lumen 16 of the tubular member 11 through the proximal end thereof until it extends through the interior of the balloon 13 so that clamping means 21 can be actuated to releasably secure the distal end of the balloon 13 to the distal end of the mandrel 20. A second hollow mandrel 22, usually much shorter than the first mandrel 20, is inserted into the inner lumen 16 through the distal end of the tubular member 11 with the proximal end of the second hollow mandrel 22 spaced distally from the distal end of the first mandrel 20. The inner guiding member 12, such as a guidewire as shown, is inserted into tubular member 11 through the first and second hollow mandrels 20 and 22 so that the region of the guiding member which is to be bonded to the tubular member 11 or the distal end of the balloon 13 is exposed between the spaced apart ends of the two hollow mandrels 20 and 22.

A two-piece threaded fitting 23 is slid over the portion of the tubular member 11 which extends over the second hollow mandrel 22. Relative axial rotation of the front piece 24 of the fitting 23 with respect to the rear piece 25 thereof tightens the distal end of the tubular member 11 onto the distal end of the second hollow mandrel 22. A knurled knob 26 is provided on the rear piece 25 to facilitate turning the fitting 23 and thus the distal end of the tubular member 11 to thereby twist the portion of the tubular member 11 which extends between the spaced apart ends of the mandrels 20 and 22.

A tensioning element 27 has a central aperture (not shown) which allows the tensioning element to fit onto the short tubular portion 28 of fitting 23. Movement of the tensioning element 27 in the direction of the arrow 30 as shown in FIG. 3 applies tension to the portion of the tubular member 11 which extends between the spaced-apart ends of the hollow mandrels 20 and 22.

As best shown in FIG. 3 the portion of the tubular member 11 which extends between the spaced-apart ends of the mandrels 20 and 22 is twisted by rotating the fitting 23 and heat is applied to the twisted portion to cause it to shrink onto the inner guiding member 12. Simultaneously, tension is applied, as indicated by the arrow 30, away from the initial position thereof, shown in phantom, to form a leak-free bond between the distal end of the balloon 13 and the inner guiding member 12.

After the twisted portion is bonded to the inner guiding member 12, it is cooled and the means releasably securing the ends of the twisted portion of tubular member 11 to the ends of the mandrels 20 and 22 are disengaged. The excess portion of the tubular member 11 which is not bonded to the inner guiding member is removed by a knife blade 31.

The number of twists given the tubular member 11, the length of the twisted section thereof and the temperature and the tension applied to the twisted tubular section during the shrinking thereof onto the inner member can be widely varied to provide a leak-free bond to the inner member, as can be appreciated by those skilled in the art depending upon the material employed. The temperature of the twisted portion of the tubular member should be controlled between the transition temperature and the melting temperature of the heat shrinkable material to heat shrink the tube. In a presently preferred embodiment, two and one-half twists and an extension of about 10% are given to the twisted portion.

The tubular member 11 can be made from heat shrinkable thermoplastic resins such as polyethelene, polyvinyl chloride and polyethelene terephthalate. The balloon member 13 can be formed from the tubular member 11 as described in U.S. Pat. No. 4,323,071 (which has been incorporated herein by reference) or the balloon can be made separately and secured to the end of the tubular member by a suitable adhesive or by shrink fitting.

The bond between the twisted distal end of the tubular member 11 or the balloon 13 is sound and can readily withstand the internal pressures encountered in angioplasty procedures, e.g. over 200 psi or more. The diameter of the bonded twisted section of the tubular member 11 is about 0.002 to about 0.006 inch (0.051–0.152 mm) less than the diameter of a conventional bond found in coronary balloon angioplasty catheters.

While the present invention has been described herein in terms of certain preferred embodiments which are directed to steerable dilatation catheters having fixed guiding members therein, it should be apparent to those skilled in the art that the present invention can be employed to bond a heat shrinkable tubular member formed of thermoplastic resins to variety of inner members. Modifications and improvements can be made to the invention without departing from the scope thereof.

What is claimed is:

1. A method for joining a section of an elongated tubular member formed of heat shrinkable thermoplastic material to an inner member extending within the tubular member comprising:
   a) inserting an end of a first mandrel into the tubular member through a proximal end of the tubular member;
   b) inserting an end of a second mandrel into the tubular member through a distal end of the tubular member, with the end of the first mandrel being axially spaced from the end of the second mandrel;
   c) positioning an inner member within the tubular member so that at least a portion thereof is disposed between the spaced-apart ends of the mandrels;
   d) releasably securing the elongated tubular member at one location to the end of the first mandrel and at a second location to the end of the second mandrel;
   e) rotating a mandrel end so that the ends of the tubular member are rotated with respect to one another and so as to twist a section of the tubular member extending between the spaced-apart ends of the mandrels;
   f) applying heat and tension to the twisted section of the tubular member to shrink the twisted section onto the inner member extending through the tubular member and to bond the twisted section thereto; and then disengaging the tubular member from the mandrel ends and removing the mandrel ends from the tubular member.

2. The method of claim 1 wherein the twisted section is heated to a temperature between the transition temperature and the melting temperature of the heat shrinkable material.

3. The method of claim 2 wherein the heat shrinkable material is selected from the group consisting of polyethylene, polyvinyl chloride and polyethylene terephthalate.

* * * * *